(12) United States Patent
Nickel

(10) Patent No.: US 11,397,232 B2
(45) Date of Patent: Jul. 26, 2022

(54) COMBINED DETERMINATION OF T1 AND A TISSUE PROPORTION

(71) Applicant: Siemens Healthcare GmbH, Erlangen (DE)

(72) Inventor: Marcel Dominik Nickel, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/124,418

(22) Filed: Dec. 16, 2020

(65) Prior Publication Data

US 2021/0181286 A1 Jun. 17, 2021

(30) Foreign Application Priority Data

Dec. 17, 2019 (DE) .......................... 102019219862.7

(51) Int. Cl.
| | |
|---|---|
| *G01R 33/54* | (2006.01) |
| *G01R 33/50* | (2006.01) |
| *G01R 33/56* | (2006.01) |
| *A61B 5/055* | (2006.01) |
| *A61B 5/00* | (2006.01) |

(Continued)

(52) U.S. Cl.
CPC ............ *G01R 33/543* (2013.01); *A61B 5/055* (2013.01); *A61B 5/7267* (2013.01); *G01R 33/50* (2013.01); *G01R 33/5608* (2013.01); *G06N 20/00* (2019.01); *G06T 11/006* (2013.01); *G16H 30/20* (2018.01); *A61B 2576/00* (2013.01); *G06T 2210/41* (2013.01); *G06T 2211/424* (2013.01)

(58) Field of Classification Search
CPC .. G01R 33/543; G01R 33/50; G01R 33/5608; G16H 30/20; G06N 20/00; A61B 5/055; A61B 5/7267; G06T 11/006
See application file for complete search history.

(56) References Cited

U.S. PATENT DOCUMENTS

| | | | | |
|---|---|---|---|---|
| 5,361,763 | A | * 11/1994 | Kao ........................ | G01R 33/56 382/145 |
| 2011/0148410 | A1* | 6/2011 | Zaitsev .............. | G01R 33/5611 324/309 |

(Continued)

OTHER PUBLICATIONS

M. Nezafat et. al.: Imaging sequence for joint myocardial T1 mapping. In: Magnetic resonance in Medicine, Band 81, Jan. 2019, pp. 486-494.

(Continued)

*Primary Examiner* — Dixomara Vargas
(74) *Attorney, Agent, or Firm* — Banner & Witcoff Ltd.

(57) ABSTRACT

In a method for determining the T1 time and also of at least one tissue proportion per voxel in a predetermined volume segment of an examination object with a magnetic resonance (MR) sequence: a radio frequency (RF) preparation pulse is radiated in; a readout module is repeatedly run after the RF preparation pulse to acquire MR data; and the T1 time and the at least one tissue proportion per voxel is determined as a function of the MR data. The readout module can include: an RF excitation pulse at a beginning of the readout module, a phase encoding gradient, and a number of readout gradients (3*a*-3*g*) for acquiring the MR data. During running of the readout module, the MR data may be acquired, at least at times, with more than two echoes.

18 Claims, 3 Drawing Sheets

(51) Int. Cl.
*G16H 30/20* (2018.01)
*G06N 20/00* (2019.01)
*G06T 11/00* (2006.01)

(56) References Cited

U.S. PATENT DOCUMENTS

| | | | |
|---|---|---|---|
| 2015/0042334 A1* | 2/2015 | Kannengiesser | G01R 33/3664 324/309 |
| 2015/0198686 A1* | 7/2015 | Paul | G01R 33/4818 324/309 |
| 2015/0338488 A1* | 11/2015 | Nittka | G01R 33/288 324/309 |
| 2017/0089999 A1* | 3/2017 | Zeller | G01R 33/5611 |
| 2017/0146631 A1* | 5/2017 | Beck | G01R 33/5608 |
| 2017/0328975 A1* | 11/2017 | Greiser | G01R 33/5673 |
| 2019/0277930 A1* | 9/2019 | Paul | G01R 33/4835 |
| 2020/0000361 A1* | 1/2020 | Zeller | G01R 33/56554 |
| 2020/0275858 A1* | 9/2020 | Mueller | G01R 33/5602 |
| 2021/0383540 A1* | 12/2021 | Kirk | G06T 7/0014 |

OTHER PUBLICATIONS

German action dated Sep. 21, 2020, Application No. 10 2019 219 862.7.

* cited by examiner

COMBINED DETERMINATION OF T1 AND A TISSUE PROPORTION

CROSS REFERENCE TO RELATED APPLICATIONS

This patent application claims priority to German Patent Application No. 10 2019 219 862.7, filed Dec. 17, 2019, which is incorporated herein by reference in its entirety.

BACKGROUND

Field

The present disclosure relates to a combined determination of the T1 time and also of a proportion of at least one species (tissue) per voxel with the same gradient echo sequence.

Related Art

Both the determination of T1 in a tissue and also the determination of a tissue proportion or a proportion of a particular species (e.g. fat or water) by means of a magnetic resonance apparatus have found their way into the classical routine. For a few medical situations (such as e.g. for multi-parametric magnetic resonance tomography of the liver) the determination of T1 and also the determination of the proportion of fat are simultaneously of interest.

According to the prior art, the determination of T1 and the determination of a specific tissue proportion (e.g. fat proportion) are undertaken using separate sequences.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
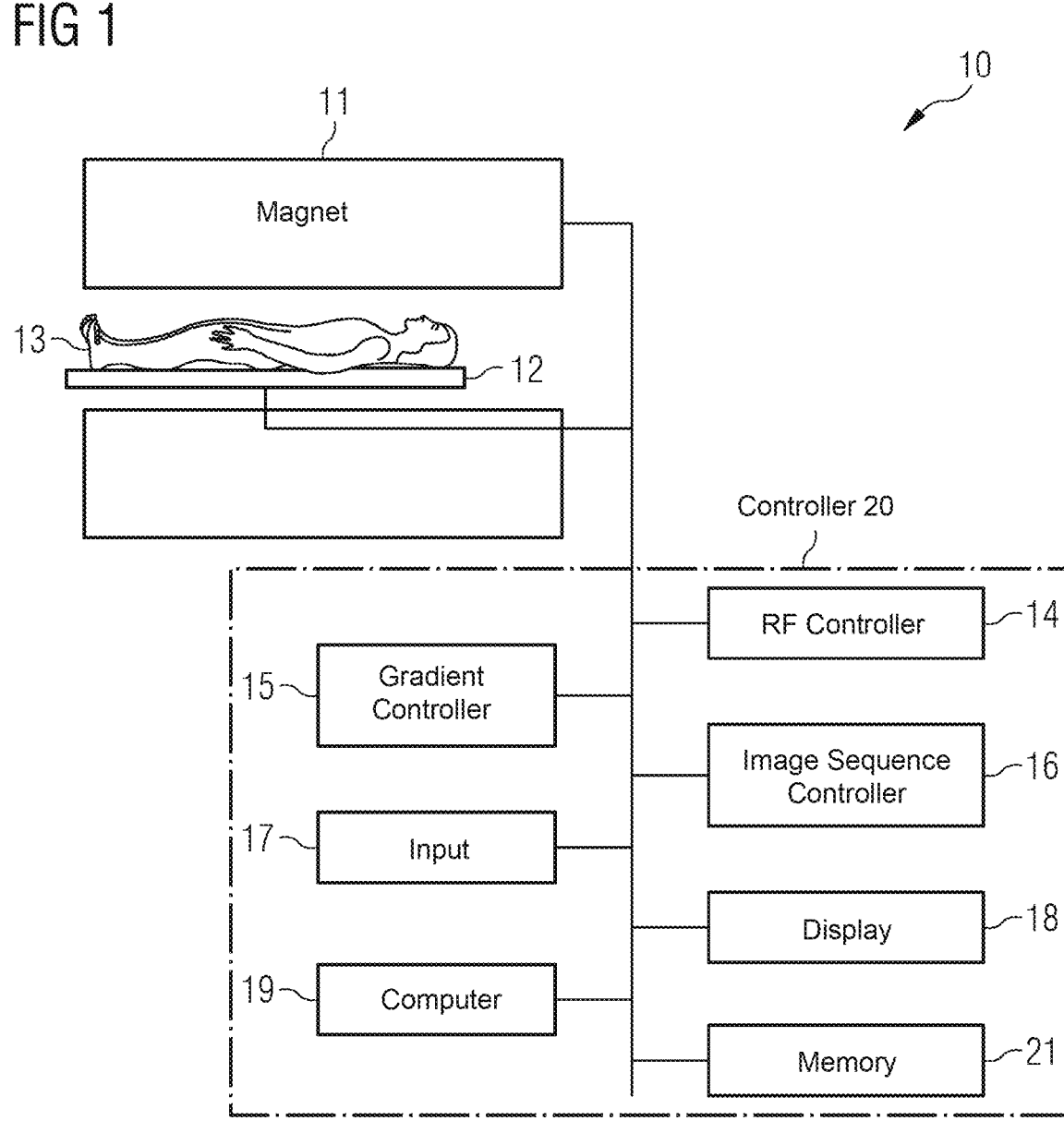
FIG. 1 shows a magnetic resonance apparatus according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

The object of the present disclosure is therefore to realize the determination of T1 and the determination of a specific tissue proportion with just one sequence.

In accordance with the disclosure this object is achieved by a method for determining the T1 time as well as at least one tissue proportion per voxel, by a magnetic resonance apparatus, by a computer program product, and by an electronically-readable data medium.

In an exemplary embodiment, a method is provided for determination of the T1 time and also of a proportion of two different species per voxel in each case in a predetermined volume segment of an examination object with (just) one MR sequence. In this case the method comprises the following steps:

Radiating in of an RF preparation pulse.

At a time after the RF preparation pulse a readout module is run a number of times in order to capture MR data thereby. In this step the readout module described in more detail below is executed a number of times consecutively. This means in particular that the (n+1)th readout module is run after the nth readout module is completed.

Depending on the MR data captured, both the T1 time per voxel and also at least one tissue proportion or the proportion of at least one species is determined per voxel. The determination of the T1 time and of the tissue proportion per voxel does not have to mean that the resolution in the determination of the T1 time is the same as the resolution in the determination of the tissue proportion, as will be explained in more detail below. While the absolute units of a tissue proportion are not defined in MR imaging, the relative ratios correspond to proton density ratios and are therefore defined quantitatively.

In this case, according to an exemplary embodiment of the disclosure, the readout module comprises:

An RF excitation pulse, which is radiated in at the beginning of the readout module. This RF excitation pulse has a flip angle, which in particular is chosen to be around the Ernst angle (i.e. the flip angle of the RF excitation pulse does not deviate from the Ernst angle by more than 5°).

One or more phase encoding gradients, which is or are switched in particular before the acquisition of the MR data.

A number of readout gradients for acquisition of the MR data. With these readout gradients the MR data per readout module is acquired with the aid of one or more echoes.

In an exemplary embodiment of the disclosure, at least a few readout modules exist within the sequence for which in each case the MR data will be acquired with the aid of more than two echoes. In other words the inventive sequence can comprise readout modules for which the MR data is acquired with only one echo and readout modules for which the MR data is acquired with precisely two echoes. It is certain however that the inventive sequence comprises at least a few readout modules for which the MR data is acquired in each case with more than two echoes.

In an exemplary embodiment of the disclosure, two variants exist for the RF preparation pulse in this case:

In the first variant the RF preparation pulse involves an RF inversion pulse that inverts the magnetization.

In the second variant the RF preparation pulse involves a saturation pulse in which the magnetization is turned not by 180° (as with the RF inversion pulse), but by 90°. In this second variant the cross magnetization in particular is additionally also spoiled or destroyed (e.g. with corresponding gradients).

The sequence according to exemplary embodiments combines a look locker sequence for determination of the T1 time with a multi-echo Dixon sequence, which acquires MR data with the aid of a number of echoes and with which at least one tissue proportion (e.g. fat proportion) can be determined.

The fact that the T1 time and the tissue proportion per voxel are acquired with just one sequence enables these parameters (T1 time, tissue proportion) to be acquired more quickly.

Since the sequence works with (only) one RF preparation pulse, the MR data is obtained at different periods of time or times after the RF preparation pulse, through which the T1 time can be determined. When the RF preparation pulse involves an RF inversion pulse, this period of time is also known as the inversion time. In other words the term period of time can be replaced by inversion time below if the RF preparation pulse involves an RF inversion pulse; i.e. the first variant described above is involved.

Although the disclosure is essentially described with a sequence with one RF preparation pulse, in accordance with the disclosure sequences are also possible which comprise a number of RF preparation pulses (a number of RF inversion pulses or a number of RF saturation pulses). When an inventive sequence comprises a number of RF preparation pulses, then the inventive sequence described with only one RF preparation pulse is repeated a number of times (as a rule with different phase encoding gradients), wherein in particular different K space areas are sampled with each repeated sequence. Thus, with an inventive sequence with a number of RF preparation pulses, more MR data can be acquired by comparison with an inventive sequence with only one RF preparation pulse, in order in this way to be able to obtain higher resolutions and/or to sample a larger volume (e.g. with 3D measurements). In this case a waiting time in particular lies after the last readout module belonging to the first, second, etc. RF preparation pulse has been run and before the radiating in of the second, third, etc. RF preparation pulse.

In accordance with the disclosure a three-dimensional or a slice-by-slice data acquisition is possible.

In an exemplary embodiment, a number or all of the following parameters can be set as a function of the period of time described above (inversion time for an RF inversion pulse). In this case this period of time specifies the period of time that has elapsed since the point in time at which the RF preparation pulse was radiated in in each case. For a sequence with a number of RF preparation pulses the period of time corresponds to the time that has elapsed since the radiating in of the last RF preparation pulse. The parameters that can be set as a function of this period of time are as follows:

The resolution during the acquisition of the MR data. With a three-dimensional MR data acquisition the spatial resolution can be set as a function of the period of time. With two-dimensional MR data acquisition the two-dimensional resolution can be set as a function of the period of time. In this case the resolution specifies in particular how many pixels or picture elements or voxels exist per unit of surface or unit of volume.

The number of echoes of the respective readout module.

The repetition time. In this case the repetition time defines the time between two consecutive RF excitation pulses.

The flip angle of the RF excitation pulse of the respective readout module.

In an exemplary embodiment, the resolution is less or lower if the period of time is small (e.g. lies below a first predetermined period threshold value, which is determined for example as a function of the average T1 time of the volume segment or corresponds to this average T1 time). In this form of embodiment the method works with a low resolution shortly after the RF preparation pulse, while later, when the relaxation curve is already approaching its steady state (e.g. state of equilibrium of a FLASH sequence), the method works with a higher resolution. Advantageously, at the beginning of the sequence, when the relaxation curve is still rising relatively sharply, this enables more MR images to be created per unit of time, in order to determine the T1 time per voxel more precisely with the aid of the image data of these MR images.

In a similar way, in an exemplary embodiment, fewer echoes are acquired per readout module when the period of time is small (e.g. lies below a second predetermined period threshold value, which is determined as a function of the average T1 time of the volume segment or corresponds to this average T1 time). When the number of echoes is small, the repetition time can also be shortened accordingly. For example with this form of embodiment just one echo can be acquired per readout module when the period of time is small. By contrast three or more echoes per readout module are acquired when the period of time lies above the average T1 time of the volume segment.

As has already been described previously in another context, the T1 time can be defined as a function of MR data that is acquired during periods of time below a third predetermined period threshold value, which is determined as a function of the average T1 time of the volume segment for example or that corresponds to this average T1 time. By contrast the proportion of the respective species can be determined as a function of MR data that is acquired during periods of time above a fourth period threshold value, which is determined as a function of the average T1 time of the volume segment for example or that corresponds to this average T1 time.

To put it another way, at the beginning of the measurement or at the beginning of the sequence the method works with a lower resolution, in order to sample the K space as quickly as possible in the phase of the rapid rise in the relaxation curve. At the beginning of the measurement the measurements are preferably taken with a Cartesian data acquisition only in the K space center and with the one radial data acquisition with only a few spokes. With the aid of this MR data acquired at the beginning of the measurement, MR images or image data the T1 times in particular are determined. Therefore the T1 times can be determined for comparatively few voxels or with a lower resolution. By contrast the tissue proportion can be determined with the aid of the MR images or image data, which is reconstructed starting from the MR data acquired at the end of the measurement or at the end of the sequence. Since the shape of the relaxation curve is flatter at the end of the measurement, the acquired MR data will be less influenced by it, which is advantageous for the determination of the tissue proportion.

In an exemplary embodiment, MR images or image data can be reconstructed from the acquired MR data at different echo times and periods. These MR images or image data reconstructed in this way are further processed by a combined signal model being adapted or fitted pixel-by-pixel. In particular the fitting of the signal model is carried out for each pixel or voxel. In this case this signal model determines a signal for each voxel as a function of the period of time, the echo time, the proportion of the respective species and the T1 time.

Then, with the aid of this adapted or fitted signal model, the T1 time and the proportion of the at least one species per voxel can be determined.

In this case the signal model in particular determines the phase of the signal. This determination of the phase necessary for determination of the respective tissue proportion can be done in this case either on the basis of all acquired MR data, or just a subset of the acquired MR data. A possible subset in this case is that MR data which is acquired in subsequent periods (e.g. period of time>average T1 time). Later periods of time and short echo times (e.g. the two first echoes of the corresponding readout module) are likewise suitable for initialization of the signal model.

When the description states that the T1 time or the tissue proportion per voxel is determined with the aid of MR data determined, then this means in particular that with the aid of this MR data determined, MR images or image data is reconstructed, as a function of which the T1 time or the tissue proportion per voxel is then determined.

In an exemplary embodiment, the previously described step of reconstruction can comprise an iterative reconstruction. In this case in the iterative reconstruction a correlation of consecutive values of a voxel over time is taken into account, which is also known as coupling of the dimensions. With the iterative reconstruction in particular, a correlation between the MR images reconstructed from the MR data is thus used, in order to improve the quality of the image data or MR images.

In a similar way it is taken into account in particular during the reconstruction that the values of neighboring pixels or voxels do not differ greatly.

Typical time conditions are suitable (TV, Wavelets, low-rank) for the periods of time (inversion times with use of an RF inversion pulse). A local low-rank regularization is suitable between image data or contrasts with different echo time. The latter prefers the local representation of a contrast image or MR image as linear combination of few independent spectral components (e.g. water, fat), as is to be expected in particular with just two types of tissue.

A suitable alternative here is a reconstruction with trained computing means (in particular a neural network (e.g. Convolutional Neural Networks (CNN))). In this case the regularizations are parameterized and the parameters have been optimized with the aid of known data.

The signal model can comprise different T1 times and/or T2* times for the different tissue or species.

It is also possible however for the T1 time and/or T2* time for the species fat to be set to a fixed value, which is determined as a function of B0 (i.e. the field strength of the basic magnetic field). In other words the T1 time and/or the T2* time can be defined for all fat pixels or fat voxels (i.e. pixels or voxels with a fat proportion of more than 50%) just as a function of B0.

In an exemplary embodiment, the signal model can comprise a strength of the B1 magnetic field per voxel, which corresponds to the actual flip angle. I.e. the signal model can comprise the actual flip angle per voxel, from which the strength of the B1 magnetic field per voxel can then be defined. In this case, in the step of fitting of the signal model, the B1 magnetic field is presumed to be spatially flat. The signal model can be smoothed and fixed after a first processing step, in order in particular to eliminate greater fluctuations in respect of the B1 magnetic field strength. A strength of the B1 magnetic field can first be determined in this case with the aid of image data of MR images with comparatively low resolution.

In an exemplary embodiment, a model-based iterative reconstruction can also be used for reconstruction of the MR images. Since in this case the signal model possesses a number of local minima, it must be insured that there is a good initialization of phase maps, the field strength of the basic magnetic field and the field strength of the B1 magnetic field. As a variant there can be an upstream conventional reconstruction for initialization so to speak.

In the model-based iterative reconstruction in particular, values such as T1, proton density of a specific species proportion, etc., per voxel (e.g. in the form of a contrast map) can be assumed and as a function of these values (e.g. by means of a Fourier transformation) K space measured values can be derived. These derived K space measured values must match the measured K space measured values as well as possible. The above-mentioned values are modified iteratively until such time as the derived K space measured values correspond to the measured K space measured values as well as possible.

In accordance with an embodiment, the signal model with which a signal of the longitudinal magnetization is specified is based on the following equation (1).

$$S_x(TI, TE) = \sum_{n=1}^{N_{species}} \left( Sp_{nx} - (\widetilde{Sp}_{n,x} + Sp_{nx})e^{\frac{TI}{T1e\!f\!f_{n,x}}} \right) c_n(TE) e^{i\varphi_x + i\omega_x TE - \frac{TE}{T^*_{2,n,x}} \pm \theta_x}, \quad (1)$$

In this equation:

$N_{species}$ corresponds to the number of the at least one tissue proportion. Therefore the sum in equation (1) sums the signal components of the different tissue when more than one tissue proportion is to be determined or $N_{species} > 1$.

$S_x$ corresponds to the signal at the voxel or pixel position x.

TE corresponds to the echo time or the time after the respective RF excitation pulse.

TI corresponds to the inversion time.

$Sp_{n,x}$ corresponds to the proton density of the state of equilibrium of a FLASH sequence of the nth tissue at the voxel or pixel position x. This state of equilibrium is also known as the steady state.

$\widetilde{Sp}_{n,x}$ corresponds to the proton densities of the nth tissue in a (thermal) steady state at the voxel or pixel position x.

$T1e\!f\!f_{n,x}$ corresponds to the effective T1 relaxation time of the nth tissue at the voxel or pixel position x.

$T^*_{2,n,x}$ corresponds to the effective $T^*_2$ relaxation time of the nth tissue at the voxel or pixel position x.

$\varphi_x$ corresponds to the phase after the RF excitation pulse at the voxel or pixel position x.

$\omega_x$ corresponds to the frequency offset at the voxel or pixel position x.

$\theta_x$ corresponds to a polarity offset at the voxel or pixel position x.

$c_n(TE)$ corresponds to the relative dephasing of the nth tissue at echo time TE through spectral displacement.

The actual T1 value and the strength of the B1 magnetic field (corresponds to the actual flip angle) can be determined in a further step from the parameters $\widetilde{Sp}_{n,x}$, $Sp_{n,x}$ and $T1eff_{n,x}$ determined.

As a rule proton densities do not have any absolute unit and contain for example factors of the transmit and receive characteristics. A relative size for a tissue proportion can be derived from the proton densities for example.

The phase $\phi_x$, the frequency offset $\theta_x$ and the polarity offset $\theta_x$ only have a slight dependency on the inversion time and can be assumed as constant per pixel or voxel.

For the fitting of the signal model multi-stage adaptations or fits can be carried out, an adaptation or a fitting of the amount of the signal can be undertaken and/or assumptions can be made about a resolution.

It has turned out that the fitting of the amount of the complex-value signal delivers robust results, whereby for example the fitting of the signal model is more stable in relation to phase errors.

In an exemplary embodiment, it is possible, during the repeated running of the readout module, to vary the flip angle and/or the repetition time. The signal model can then be simulated for this varying flip angle and/or for the varying repetition time and fitted to the reconstructed image data. This image data is reconstructed in this case starting from the MR data, which is acquired with the inventive sequence, which in this case has a varying flip angle and/or a varying repetition time.

When the inventive sequence has a varying flip angle and/or a varying repetition time the signal model cannot always be specified as a closed analytical formula. However there are also established methods for this form of embodiment, which allow a fitting of the reconstructed image data to model parameters. An example of this is MR fingerprinting.

Within the framework of the present disclosure a magnetic resonance apparatus is also provided, which comprises an RF controller, a gradient controller, an image sequence control and a computing unit, which is embodied to determine T1 and also a proportion of at least one species determined (at least one tissue proportion) in a predetermined volume segment within an examination object. The magnetic resonance apparatus is embodied to radiate in an RF preparation pulse, to run a readout module repeatedly after the RF preparation pulse, to acquire MR data, and to determine T1 and also the proportion of one or more species as a function of the MR data. In this case each readout module comprises an RF excitation pulse at the beginning of the readout module, one or more phase encoding gradients and a number of readout gradients for acquiring the MR data. In this case the MR data is acquired at least some of the time when the respective readout module is run with more than two echoes.

The advantages of the inventive magnetic resonance apparatus essentially correspond to the advantages of the inventive method, which have been described above in detail, so that any further description will be dispensed with here.

Furthermore the present disclosure describes a computer program product, in particular software, which can be loaded into a memory of a programmable control device or a computing unit of a magnetic resonance apparatus. All or various forms of embodiment of the inventive method described above can be carried out with this computer program product when the computer program product is running in the control device. In such cases the computer program product might possibly need program means, e.g. libraries and auxiliary functions, in order to realize the corresponding forms of embodiment of the method. In other words, aspects directed to the computer program product is intended in particular to protect software with which one of the forms of embodiment of the inventive method described above can be carried out or which carries out this form of embodiment. In this case the software can involve source code (e.g. C++) that still needs to be compiled and linked or that only has to be interpreted, or can involve executable software code that only has to be loaded into a corresponding computing unit or control device to execute it.

In an exemplary embodiment, an electronically-readable data medium, e.g. a DVD, a magnetic tape, a hard disk or a USB stick, on which electronically-readable control information, in particular software (cf. above), is stored. When this control information (software) is read from the data medium and stored in a control device or computing unit of a magnetic resonance apparatus, all inventive forms of the method described above can be carried out.

With the present disclosure, with one or the same sequence, both the T1 time per voxel and also a proportion of at least one species determined per voxel can be determined. To put it another way, the present disclosure, with just one measurement or just one sequence, creates a parameter map, which specifies which pixel or voxel has which tissue proportion (e.g. fat proportion) and which T1 time.

A T1 measurement is influenced by the fat proportion for example. In a similar way the T1 time influences the measurement of the fat proportion for example. Therefore a combined measurement of the T1 time and a tissue proportion (e.g. fat) can deliver more precise results than two individual measurements for determination of the T1 time or the determination of a tissue proportion, since the combined measurement takes account of the mutual influence of the T1 time and of the tissue proportion in the determination.

With regard to FIG. 1 a magnetic resonance apparatus 10 is shown, with which, as will be explained below, in accordance with the disclosure, the T1 time as well as the proportion of at least one species per voxel is determined with the same sequence. The magnetic resonance apparatus 10 includes a scanner that having a magnet 11 to create a polarization field B0, wherein a person to be examined 13 arranged on a couch 12 is moved into the magnet 11 in order to record spatially-encoded magnetic resonance signals or MR data from the person being examined 13. The coils being used for signal recording such as a whole body coil or local coils are not shown for reasons of clarity. By radiating in radio frequency pulses and switching magnetic field gradients, the magnetization created by the polarization field B0 can be deflected from the steady state and spatially encoded, and the magnetization produced detected by the receive coils. How MR images can be created by radiating in the RF pulses and by switching magnetic field gradients in various combinations and sequences is fundamentally known to the person skilled in the art and will not be explained in any greater detail here.

In an exemplary embodiment, the magnetic resonance apparatus 10 furthermore has a controller 20, which can be used for controlling the magnetic resonance apparatus 10. The controller 20 has a gradient controller 15 for controlling and switching the necessary magnetic field gradients. An RF controller 14 is intended for the control and generation of the RF pulses for deflecting the magnetization. An image sequence controller 16 controls the sequence of the magnetic field gradients and RF pulses and thus indirectly the gradient controller 15 and the RF controller 14. Via an input unit 17 an operator can control the magnetic resonance apparatus 10 and MR images and other information for control can be displayed on a display unit 18. A computer 19 with at least one processor unit (not shown) is provided for control of the various units in the controller 20 and to carry out computing operations. Furthermore a memory unit 21 is provided, in which for example program modules or programs can be stored, which, when they are executed by the computer 19 or its processor unit, can control the execution sequence of the magnetic resonance apparatus 10. The computer 19 is embodied to compute the MR images from the acquired MR signals. In an exemplary embodiment, the controller 20 (and/or one or more of its components) includes processor circuitry that is configured to perform one or more functions and/or operations of the controller 20 (or of the respective component(s)).

Figure 2:
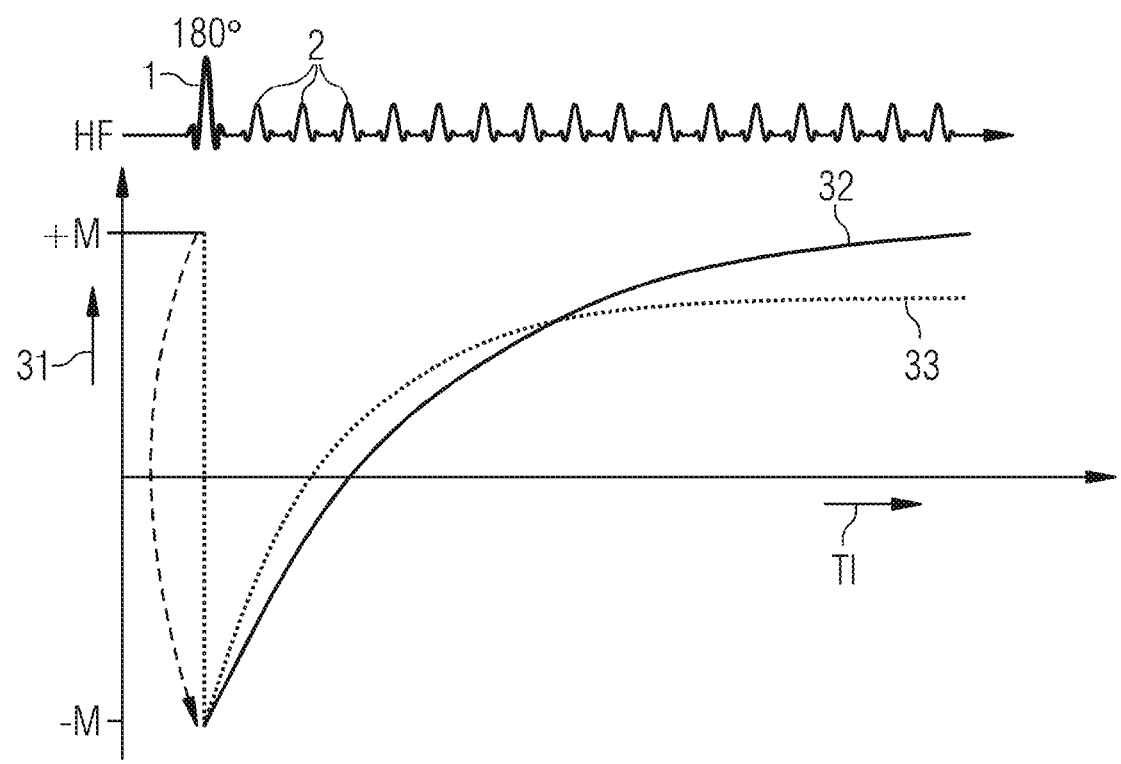
FIG. 2 shows a plot comparing methods for T1 determination according to an exemplary embodiment.

The inventive method for determination of the T1 time is compared with a further method in FIG. 2.

If only one RF inversion pulse 1 (and no following RF excitation pulses 2) is radiated in, the magnetization relaxes according to the Bloch equation with what is known as the true relaxation time T1 (True T1), as is shown by the curve 32 in FIG. 2. Because of the slow relaxation a direct determination of the T1 time with the aid of the curve 32 would take a very long time.

To speed up the process RF excitation pulses 2 are radiated in continuously with a fixed repetition time TR typically with flip angles around the Ernst angle. With this type of sequence the core magnetization for each excitation pulse can be destroyed by gradients and RF spoiling. In this case the longitudinal magnetization relaxes in a similar way to the free magnetization, but with a different effective T1 time (apparent T1) compared to the true T1 time and to a different steady state, as is shown with the aid of curve 33 in FIG. 2. The determination of the effective T1 time with the aid of the curve 33 then also enables the true T1 time per voxel to be computed or determined by means of a signal model.

Figure 3:
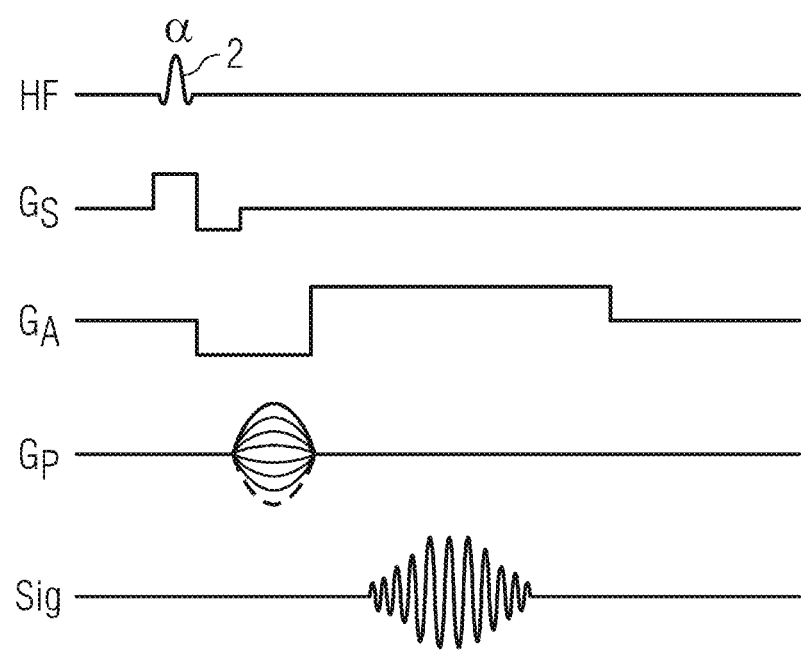
FIG. 3 shows a plot of a readout of a sequence for T1 determination according to an exemplary embodiment.

Shown in FIG. 3 is an example of a readout module of a sequence for determination of the (effective) T1 time per voxel.

A slice selection gradient $G_S$ is switched at the same time as the RF excitation pulse 2 with the flip angle α. Subsequently at least one phase encoding gradient $G_P$ and a readout gradient $G_A$ are switched, which are followed by a further readout gradient $G_A$, during which the signal Sig is acquired.

With the readout module shown in FIG. 3 the MR data of one K space row can be acquired. If for example 50 to 100 readout modules are run for a two-dimensional measurement (or over 1000 readout modules for a three-dimensional measurement), an MR image can be computed or reconstructed with the aid of the MR data acquired by them.

When the repetition time TR lies at 3 ms for example and 60 repetitions or measurements are needed for an MR image, the MR data for an MR image can be acquired in less than 200 ms. Typical T1 times lie at around 1 s, wherein the relaxation curve is sampled for around 3 s. Assuming that the relaxation curve does not change greatly during 200 ms and the reconstructed contrast corresponds to the time of the measurement of the K space center, MR data for approximately 16 MR images can be acquired with one sequence (i.e. during one relaxation).

With the aid of the image data reconstructed or computed by this method the T1 times can then be determined for all voxels, so that advantageously only one inventive sequence is required for determination of the T1 times for all voxels.

Figure 4:
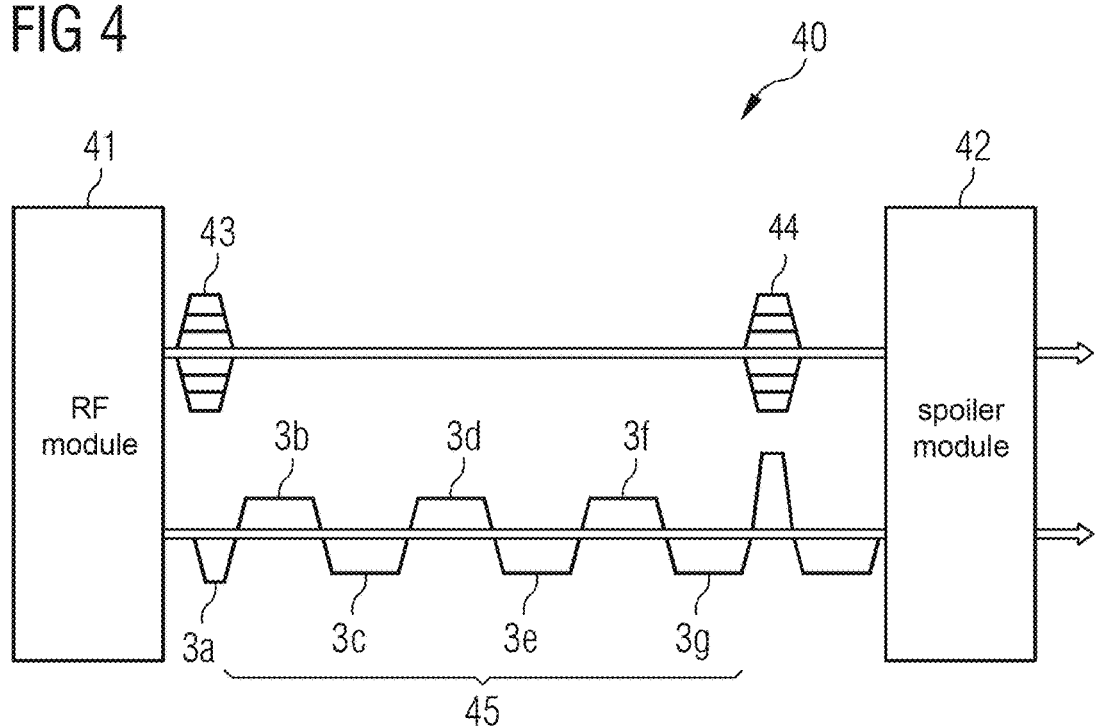
FIG. 4 shows a plot of a readout of a sequence for T1 determination according to an exemplary embodiment.

Now, for separation of different species (e.g. water and fat), instead of the readout module 40 shown in FIG. 3, the readout module 40 shown in FIG. 4 is used, in which MR data is acquired for a number of echoes or echo times, as is usual with the Dixon method. In the Dixon method the fact that after the RF excitation pulse (in RF module 41) the protons of the one species are rotating at a different speed compared to the protons of another species is exploited, i.e. the corresponding Larmor frequencies are different. By utilizing the knowledge of these relative rotation speeds of e.g. two species, in accordance with the Dixon method the proportion of at least one of these species per voxel can be determined.

In the readout module 40 shown in FIG. 4, after the RF module 41 a phase encoding 43 takes place, wherein at the same time as this phase encoding 43 a first readout gradient 3a is switched. Subsequently six readout gradients 3b-3g follow each other, during which in each case MR data (e.g. of the same K space row) is acquired. After the acquisition 45 of the MR data, through the switching of a further phase encoding gradient 44 the phase encoding is reset again so to speak as a result of the phase encoding gradient 43. At the end of each readout module 40 a spoiler module 42 is run in order to eliminate disruptive magnetization.

Then for example, with the aid of the MR data acquired during a number of echoes and thus in different phases, an in-phase MR image (the spins of the two species are in phase) and an out-of-phase MR image (the phases of the spins of the two species are offset by 180°) can be created, wherein with the aid of the image data of these MR images the proportion of at least one of the two species per voxel can be determined in each case.

The acquisition of more than two echoes per readout module, by contrast with an acquisition of only two echoes, has the advantage that in some respects more than two measurement points are present, so that the precision in the determination of the tissue proportion is better.

Figure 5:
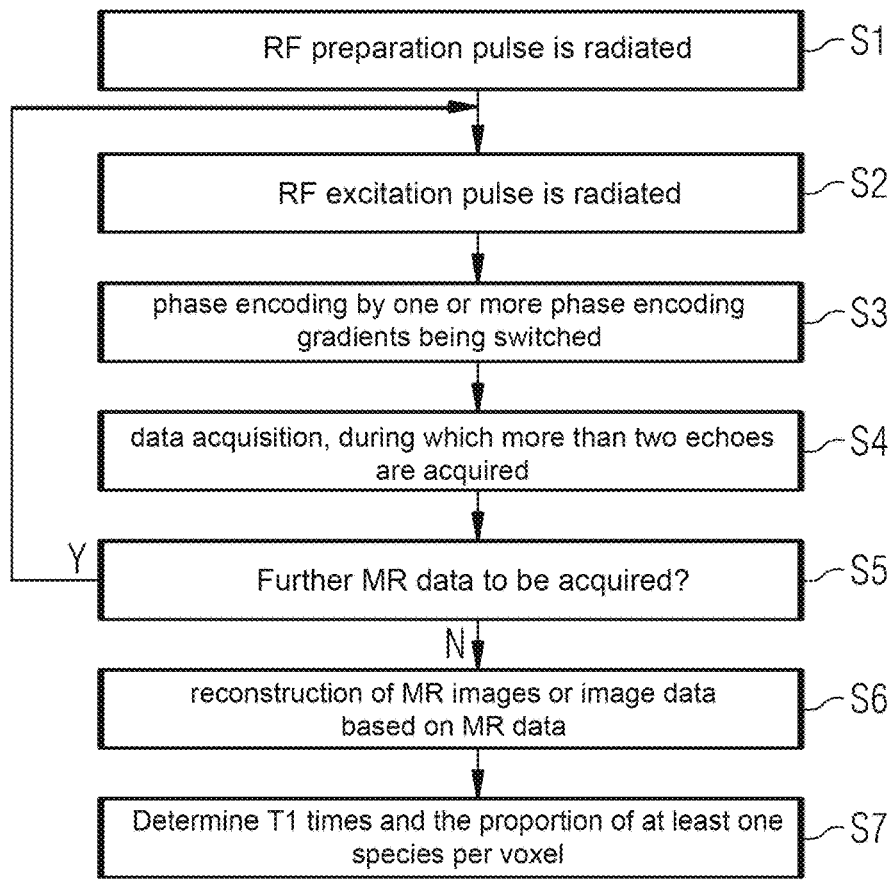
FIG. 5 is a flowchart of a method for simultaneous determination of T1 and also of a proportion of at least one species per voxel according to an exemplary embodiment.

Shown in FIG. 5 is the flow diagram of an inventive method for simultaneous determination of the T1 time and also of a proportion of at least one species per voxel.

In this figure, in a first step S1 an RF preparation pulse is radiated in. This step S1 is followed by a step S2, in which an RF excitation pulse is radiated in. In subsequent step S3 there is a phase encoding by one or more phase encoding gradients being switched. This is followed, in step S4, by data acquisition, during which more than two echoes are acquired. The steps S2 to S4 in this case essentially correspond to the readout module 40 shown in FIG. 4.

In step S5 a check is carried out as to whether further MR data (e.g. further K space rows) are to be acquired. If this is the case, the inventive method branches to S2, while otherwise the inventive method is continued with step S6. In this step S6 there is a reconstruction of MR images or image data with the aid of the MR data previously acquired in step S4. Through the fitting of a corresponding signal model both the T1 times and also the proportion of at least one species per voxel are determined in step S7.

Although it is not shown, it is possible in accordance with the disclosure to branch from the decision step S5 to the step S1 in order to radiate in a further RF preparation pulse, which is then once again followed by a repeated running of the steps S2 to S5, as a rule with different phase encoders. This process can be repeated any number of times until a sufficient amount of MR data has been acquired.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for determining a T1 time and at least one tissue proportion per voxel in a predetermined volume segment of an examination object with a magnetic resonance (MR) sequence, the method comprising:
   radiating in of a radio frequency (RF) preparation pulse;
   repeatedly running of a readout module after the RF preparation pulse to acquire MR data, the readout module including: an RF excitation pulse at a beginning of the readout module, a phase encoding gradient, and a number of readout gradients for acquiring the MR data, wherein during running of the readout module, the MR data is acquired, at least at times, with more than two echoes; and
   determining the T1 time and the at least one tissue proportion per voxel as a function of the MR data.

2. The method as claimed in claim 1, wherein the RF preparation pulse is an RF inversion pulse or an RF saturation pulse.

3. The method as claimed in claim 1, wherein at least one of the following parameters is set differently as a function of a period of time that has elapsed since the radiating in of the RF preparation pulse:
   a resolution during the acquisition of the MR data,
   a number of echoes of the respective readout module,
   a repetition time, and
   a flip angle of the RF excitation pulse of the respective readout module.

4. The method as claimed in claim 3, wherein the resolution decreases as the period of time decreases.

5. The method as claimed in claim 3, wherein the number of echoes decreases as the period of time decreases.

6. The method as claimed in claim 1, wherein:
   the T1 time is determined as a function of MR data that is acquired during periods of time below a period threshold value, and the at least one tissue proportion is determined as a function of MR data that is acquired during periods of time above a period threshold value.

7. The method as claimed in claim 1, further comprising:
reconstructing image data from the MR data acquired at different echo times and periods of time; and
fitting, pixel-by-pixel, a combined signal model based on the reconstructed image data to determine a signal per voxel as a function of the period of time, the echo time, the at least one tissue proportion, and the T1 time.

8. The method as claimed in claim 7, wherein:
the reconstruction of the image data comprises an iterative reconstruction, and
a correlation of consecutive values of the image data of a voxel is considered in the iterative reconstruction.

9. The method as claimed in claim 7, wherein the reconstruction of the image data is carried out with a computer that is optimized to training data, in which a number of items of image data are correlated.

10. The method as claimed in claim 7, wherein the signal model comprises different T1 times and/or T2* times for the various tissues.

11. The method as claimed in claim 10, wherein the T1 time and/or T2* time for a fat proportion is set to a fixed value that depends on a field strength of the basic magnetic field of a magnetic resonance apparatus.

12. The method as claimed in claim 7, wherein:
the signal model comprises a strength of s B1 magnetic field of a magnetic resonance apparatus per voxel, and when the signal model is fitted, the B1 magnetic field is presumed to be spatially smooth.

13. The method as claimed in claim 7, wherein the reconstruction of the images comprises a model-based iterative reconstruction.

14. The method as claimed in claim 7, wherein the signal model is based on the following equation:

$$S_x(TI, TE) = \sum_{n=1}^{N_{species}} \left(Sp_{n,x} - (\widetilde{Sp}_{u,x} + Sp_{n,x})e^{-\frac{TI}{T1\mathit{eff}_{n,x}}}\right)c_n(TE)e^{i\varphi_x + i\omega_x TE - \frac{TE}{T^*_{2,n,x}} \pm \theta_x}, \quad (1)$$

wherein:
$N_{species}$ corresponds to a number of the at least one tissue proportion,
$S_x$ corresponds to the signal at the voxel or pixel position x,
TE corresponds to the echo time or the time after the respective RF excitation pulse,
TI corresponds to the inversion time,
$Sp_{n,x}$ corresponds to proton densities of a steady state of a Fast Low Angle Shot (FLASH) sequence of the nth tissue at the voxel or pixel position x,
$\widetilde{Sp}_{n,x}$ corresponds to the proton densities of the nth tissue in the steady state at the voxel or pixel position x,
$T1\mathit{eff}_{n,x}$ corresponds to an effective T1 relaxation time of the nth tissue at the voxel or pixel position x,
$T^*_{2,n,x}$ corresponds to an effective $T^*_2$ relaxation time of the nth tissue at the voxel or pixel position x,
$\varphi_x$ corresponds to a phase after the RF excitation pulse at the voxel or pixel position x,
$\omega_x$ corresponds to a frequency offset at the voxel or pixel position x,
$\theta_x$ corresponds to a polarity offset at the voxel or pixel position x, and
$c_n(TE)$ corresponds to a relative dephasing of the nth tissue at echo time TE through spectral displacement.

15. The method as claimed in claim 7, wherein:
during the repeated running of the readout module, the flip angle and/or the repetition time is/are varied, and
the signal model is simulated for a varying flip angle and/or a varying repetition time and is fitted to the reconstructed image data.

16. A computer program product which includes a computer program and is directly loadable into a memory of a controller of a magnetic resonance apparatus, when executed by the controller, causes the controller to perform the method as claimed in claim 1.

17. A non-transitory computer-readable storage medium with an executable program stored thereon, that when executed, instructs a processor to perform the method of claim 1.

18. A magnetic resonance (MR) apparatus for determination of a T1 time and at least one tissue proportion per voxel in a predetermined volume segment of an examination object with an MR sequence, the MR apparatus comprising:
a scanner; and
a controller including an RF controller, a gradient controller, an image sequence controller; and a computer, the controller being configured to:
radiate in an RF preparation pulse;
run a readout module repeatedly after the RF preparation pulse to acquire MR data, the readout module including: an RF excitation pulse at a beginning of the readout module, a phase encoding gradient, and a number of readout gradients for acquiring the MR data, wherein at least at times during the running of the readout module, the MR data is acquired with more than two echoes; and
determine the T1 time and the at least one tissue proportion per voxel as a function of the MR data.

* * * * *